United States Patent
Kato et al.

(10) Patent No.: US 7,708,692 B2
(45) Date of Patent: May 4, 2010

(54) ULTRASONIC DIAGNOSTIC APPARATUS AND METHOD FOR CONTROLLING THE SAME

(75) Inventors: Makoto Kato, Yokohama (JP); Kazuhiro Sunagawa, Sendai (JP)

(73) Assignee: Panasonic Corporation, Kadoma (JP)

( * ) Notice: Subject to any disclaimer, the term of this patent is extended or adjusted under 35 U.S.C. 154(b) by 1114 days.

(21) Appl. No.: 11/224,265

(22) Filed: Sep. 12, 2005

(65) Prior Publication Data

US 2006/0004288 A1 Jan. 5, 2006

Related U.S. Application Data

(63) Continuation of application No. PCT/JP2005/009162, filed on May 19, 2005.

(30) Foreign Application Priority Data

May 21, 2004 (JP) .............................. 2004-151689

(51) Int. Cl.
*A61B 8/00* (2006.01)
(52) U.S. Cl. ...................................... 600/438; 600/449
(58) Field of Classification Search ................. 600/438, 600/441, 450, 453, 468, 457, 437, 449, 459, 600/463
See application file for complete search history.

(56) References Cited

U.S. PATENT DOCUMENTS 5,107,840 A * 4/1992 Bonnefous ................... 600/454
5,840,028 A 11/1998 Chubachi et al.
2001/0016686 A1 * 8/2001 Okada et al. ................. 600/454
2003/0009101 A1 * 1/2003 Sunagawa et al. ............ 600/437

FOREIGN PATENT DOCUMENTS

EP 1 273 267 1/2003

(Continued)

OTHER PUBLICATIONS

Supplementary European Search Report for corresponding Application No. EP 05 74 0921 dated Jul. 6, 2009.

(Continued)

*Primary Examiner*—Brian Casler
*Assistant Examiner*—Elmer Chao
(74) *Attorney, Agent, or Firm*—Renner, Otto, Boisselle & Sklar, LLP

(57) ABSTRACT

An ultrasonic diagnostic apparatus includes: a transmitting section for driving an ultrasonic probe sending out an ultrasonic transmitted wave toward a body tissue of an organism; a receiving section for receiving an ultrasonic reflected wave, produced by getting the transmitted wave reflected by the body tissue, through the probe; a phase detecting section for detecting the phase of the reflected wave; and a computing section for calculating the magnitudes of positional displacement at multiple measuring points on the body tissue based on a signal obtained by the detecting section and calculating the greatest thickness difference between two of the measuring points and/or an elastic property based on the magnitudes of positional displacement. The computing section calculates the maximum and minimum thicknesses or thickness variations between the two points based on the magnitudes of positional displacement at the two points during a part of one cardiac cycle, and calculates the greatest thickness difference and/or elastic property as the difference between the maximum and minimum values.

18 Claims, 5 Drawing Sheets

FOREIGN PATENT DOCUMENTS

| | | |
|---|---|---|
| EP | 1 421 905 | 5/2004 |
| JP | 62-266040 | 11/1987 |
| JP | 10-005226 | 1/1998 |
| JP | 2000-229078 | 8/2000 |
| JP | 2000-333955 | 12/2000 |
| JP | 2001-292995 | 10/2001 |
| JP | 2002-209857 | 7/2002 |

OTHER PUBLICATIONS

Hoeks et al., "Assessment of the Distensibility of Superficial Arteries", Ultrasound in Medicine and Biology, New York, NY, vol. 16, No. 2, Jan. 1, 1990, pp. 121-128, XP023259461.

* cited by examiner

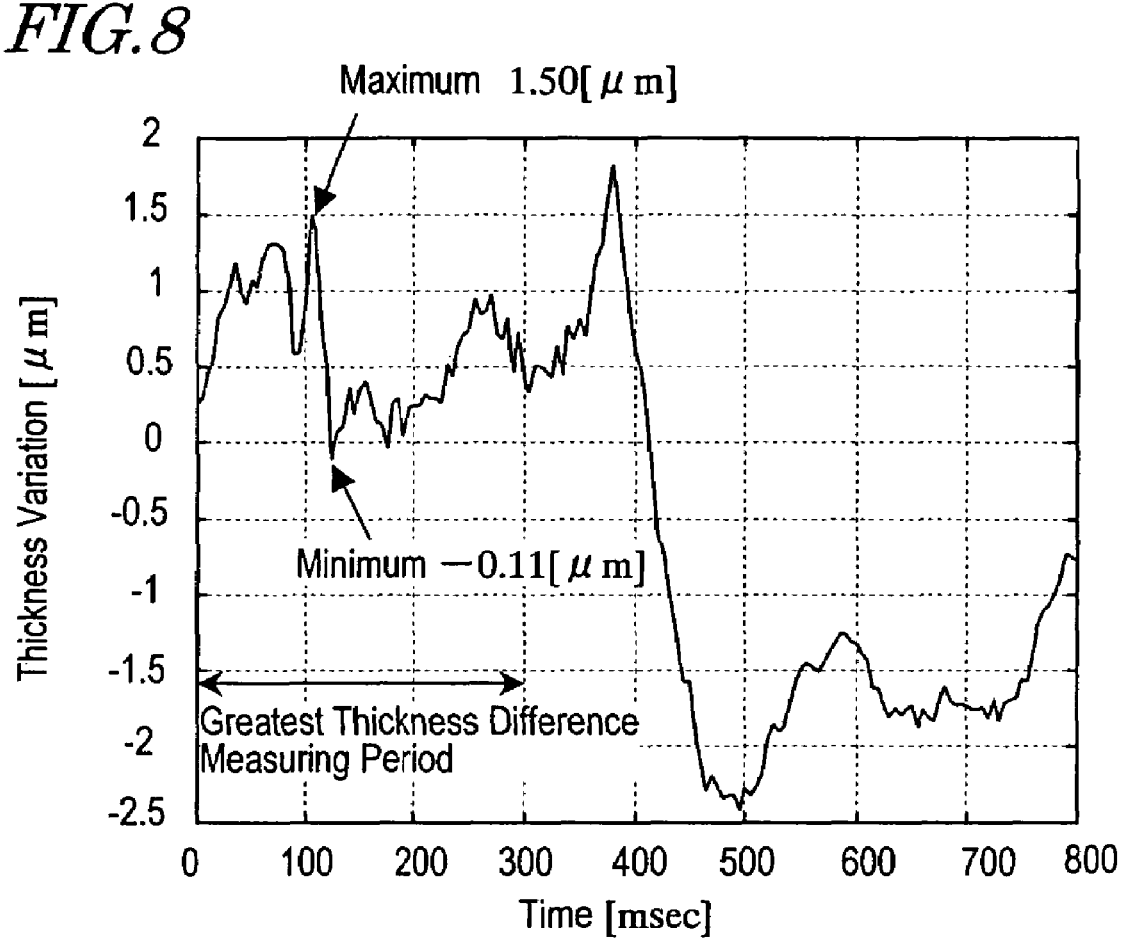

ULTRASONIC DIAGNOSTIC APPARATUS AND METHOD FOR CONTROLLING THE SAME

This is a continuation of International Application PCT/JP2005/009162, with an international filing date of May 19, 2005.

FIELD OF THE INVENTION

The present invention relates to an ultrasonic diagnostic apparatus for measuring the elastic property of a vital tissue using an ultrasonic wave and also relates to a method for controlling such an ultrasonic diagnostic apparatus.

DESCRIPTION OF THE RELATED ART

Recently, the number of people suffering from various circulatory system diseases, including heart infarction and brain infarction, has been on the rise, thus making it more and more urgent to prevent and treat these diseases.

The pathopoiesis of heart or brain infarction is closely correlated to arterial sclerosis. More specifically, if an atheroma is created on the arterial wall or if no arterial cells are produced anymore due to various factors such as elevated blood pressure, then the artery loses its elasticity to become hard and fragile. Also, if the blood vessel is clogged up where the atheroma has been created or if a vascular tissue covering the atheroma has ruptured, then the atheroma will move itself into the blood vessel to clog up the artery elsewhere or to rupture the hardened portions of the artery. As a result, these diseases are caused. That is why it is important to diagnose the arterial sclerosis as early as possible to prevent or treat these diseases.

If the arterial sclerosis can be diagnosed early enough to administer some medicine to its patient, then the disease can be treated effectively. However, it is said that once the arterial sclerosis has advanced to a certain degree, the farther advancement of that disease can be checked with the administration of medicine but it is difficult to repair the hardened artery completely.

In the prior art, the lesion of arterial sclerosis is diagnosed by directly observing the inside of the blood vessel with a vascular catheter. However, this diagnosis needs to be carried out with a vascular catheter inserted into the blood vessel of a patient, thus imposing a heavy load on him or her. For that reason, the vascular catheter observation is usually adopted to locate the lesion of arterial sclerosis in a patient who is already known to suffer from that disease but has never been used to make a medical checkup on a supposedly healthy person.

A checkup may be easily made without imposing excessively heavy load on a patient if the index of cholesterol, which is one of major causes of arterial sclerosis, or the blood pressure is measured. However, none of these values directly indicates the degree of advancement of arterial sclerosis.

That is why a method or apparatus for diagnosing the arterial sclerosis at an early stage of its advancement without imposing too much load on its patient is now in high demand.

An ultrasonic diagnostic apparatus has been used in the prior art as a medical apparatus that imposes only a light load on its patient. Specifically, by irradiating the patient with an ultrasonic wave that has been produced externally by the ultrasonic diagnostic apparatus, geometric information, mobility information or quality information of his or her internal body can be acquired without causing pain to him or her.

Among other things, if ultrasonic measurement is carried out on an object, then mobility information of the object can be acquired. Thus, the elastic property of the object can be estimated by the magnitude of positional displacement of the object. That is to say, in this case, the elastic property of the blood vessel of an organism can be evaluated and the degree of advancement of arterial sclerosis can be known directly. On top of that, the measurement can be done just by putting an ultrasonic probe on a patient, and very little load is placed on him or her. For that reason, if the ultrasonic diagnostic apparatus is used, the arterial sclerosis could be diagnosed accurately and a preventive checkup could be carried out on a person under measurement without imposing excessive load on him or her.

However, conventional ultrasonic diagnostic apparatuses, including one for observing the shape of an embryo or making auscultation on his or her heartbeat, do not usually achieve sufficiently high resolutions in terms of geometric information and mobility information. That is why it is impossible to figure out the elastic property of an artery, which expands and shrinks in sync with a cardiac cycle, using a conventional ultrasonic diagnostic apparatus. For example, as disclosed in Japanese Patent Application Laid-Open Publication No. 62-266040, most of conventional ultrasonic diagnostic apparatuses cannot measure the displacement of the object sufficiently accurately.

Recently, however, some ultrasonic diagnostic apparatuses can have significantly improved measuring accuracy thanks to remarkable advancement of electronic technologies. As a result, ultrasonic diagnostic apparatuses for measuring the very small motion of a vital tissue have been developed. For example, Japanese Patent Application Laid-Open Publication No. 10-5226 discloses an ultrasonic diagnostic apparatus for tracking the phase with high accuracy by determining the instantaneous location of an object by a restricted minimum square method using both the amplitude and phase of a detection signal. This apparatus can measure the very small vibration of a tissue that is moving greatly due to pulsations. According to Japanese Patent Application Laid-Open Publication No. 10-5226, the very small vibrations with frequencies of several hundreds of Hz or less, which are included in a displacement motion caused by a pulsation with a huge amplitude of 10 mm or more, can be measured with good enough reproducibility even if the pulsations are repeated about 10 times.

The apparatuses disclosed in Japanese Patent Application Laid-Open Publication No. 10-5226 and Japanese Patent Application Laid-Open Publication No. 2000-229078 can measure high frequency components up to several hundreds of Hz with good reproducibility and converge an ultrasonic beam, thereby evaluating the elastic property of an area with a diameter of about 1 to 2 mm on a cardiac muscle or arterial wall. In addition, those apparatuses are reported to have excellent features in that the apparatuses can obtain an ultrasonic signal with a component of any time phase and can analyze the frequency spectrum of that signal during one cardiac cycle.

Therefore, an ultrasonic diagnostic apparatus according to the techniques disclosed in these documents is expected to check the degree of advancement of arterial sclerosis with time without imposing heavy load on a person under a physical checkup, for example, and eventually prevent any disease caused by the arterial sclerosis. The apparatus is also expected to locate a region where the blood vessel ruptures easily and to treat that region by measuring the elastic property of a very small area of the artery.

As described above, in evaluating the elastic property of a substance using an ultrasonic wave, the mobility information of the object under measurement is acquired. Suppose the elastic property of a vital tissue (e.g., the elastic property of a vascular wall, among other things) should be evaluated one cardiac cycle after another. In that case, the elastic property E of the vascular wall may be given by:

$$E = \Delta p \cdot H / \Delta h$$

where $\Delta p$ is the difference between the maximum and minimum blood pressure values, $\Delta h$ is the greatest thickness difference of the vascular wall during an arbitrary cardiac cycle, and H is the maximum thickness of the vascular wall.

Among these values, the maximum and minimum blood pressure values are obtained by measuring the blood pressure with a blood pressure manometer, for example. Meanwhile, the greatest thickness difference $\Delta h$ of the vascular wall is calculated based on the maximum and minimum thickness variations of the vascular wall as measured by the method of Japanese Patent Application Laid-Open Publication No. 10-5226 mentioned above, for example.

However, if some noise, of which the magnitude exceeds the maximum and minimum thickness variations, were caused during the ultrasonic wave measurement, then a wrong greatest thickness difference, different from its actual value, would be obtained in error and the elastic property could not be evaluated properly.

What is more, this computation needs to be carried out by a computer of which the processing performance is much higher than that of a conventional ultrasonic diagnostic apparatus for displaying the shape of a vital tissue. That is why the overall price of an apparatus including such a high-performance computer goes rather high. Nevertheless, if a computer with just moderate processing performance is used, then it will take a lot of time to get the computations done, thus causing a time lag before presenting the results of measurement.

SUMMARY OF THE INVENTION

In order to overcome at least one of these problems, an object of the present invention is to provide an ultrasonic diagnostic apparatus that can accurately measure the elastic property with the influence of noise minimized.

An ultrasonic diagnostic apparatus according to the present invention includes: a transmitting section for driving an ultrasonic probe that sends out an ultrasonic transmitted wave toward a body tissue of an organism; a receiving section for receiving an ultrasonic reflected wave through the ultrasonic probe, the ultrasonic reflected wave being produced by getting the ultrasonic transmitted wave reflected by the body tissue; a phase detecting section for detecting the phase of the ultrasonic reflected wave; and a computing section for calculating the magnitudes of positional displacement at a plurality of measuring points on the body tissue based on a signal obtained by the phase detecting section and also figuring out the greatest thickness difference between two of the measuring points and/or an elastic property based on the magnitudes of positional displacement. The computing section figures out either the maximum and minimum thicknesses or thickness variations between the two points based on the magnitudes of positional displacement at the two points during a partial period of one cardiac cycle of the organism, and also calculates the greatest thickness difference and/or elastic property as the difference between the maximum and minimum values.

In a preferred embodiment, the body tissue is a circulatory organ, and the computing section receives information about a blood pressure value of the organism and figures out the elastic property based on the blood pressure value.

In another preferred embodiment, the partial period of the one cardiac cycle is set in sync with a biomedical signal obtained from the organism.

In a specific preferred embodiment, the biomedical signal is represented as an electrocardiogram by an electrocardiograph.

In this particular preferred embodiment, the partial period of the one cardiac cycle is set based on at least one of P, Q, R, S, T and U waves of the electrocardiogram.

In an alternative preferred embodiment, the partial period of the one cardiac cycle is set based on the R and T waves of the electrocardiogram.

In still another preferred embodiment, the biomedical signal is represented as a phonocardiogram by a phonocardiograph.

In this particular preferred embodiment, the partial period of the one cardiac cycle is set based on at least one of I, II, III and IV sounds of the phonocardiogram.

In yet another preferred embodiment, the biomedical signal is represented as a sphygmogram by a sphygmograph.

In this particular preferred embodiment, the partial period of the one cardiac cycle is set based on at least one of S, P, T, C and D waves of the sphygmogram.

In yet another preferred embodiment, the computing section calculates in advance a positional displacement waveform, showing the magnitude of positional displacement of the body tissue during the one cardiac cycle, and sets the partial period of the one cardiac cycle based on the positional displacement waveform.

In yet another preferred embodiment, the computing section calculates in advance a thickness variation waveform, showing a variation in the thickness of the body tissue during the one cardiac cycle, according to the magnitude of positional displacement and sets the partial period of the one cardiac cycle based on the thickness variation waveform.

In yet another preferred embodiment, the computing section calculates in advance a vascular caliber variation waveform, showing a variation in the vascular caliber of the body tissue during the one cardiac cycle, according to the magnitude of positional displacement and sets the partial period of the one cardiac cycle based on the vascular caliber variation waveform.

In yet another preferred embodiment, the partial period accounts for 5% to 75% of the one cardiac cycle.

In yet another preferred embodiment, the ultrasonic diagnostic apparatus further includes a display section for displaying the greatest thickness difference and/or elastic property. The computing section calculates the greatest thickness difference and/or elastic property during the rest of the one cardiac cycle after the partial period has expired. And the display section starts to display the greatest thickness difference and/or elastic property during the one cardiac cycle including the partial period.

In this particular preferred embodiment, the transmitting section drives the ultrasonic probe during the partial period of the one cardiac cycle and stops driving the ultrasonic probe during the rest of the one cardiac cycle.

A method for controlling an ultrasonic diagnostic apparatus according to the present invention is carried out by the control section of the apparatus. The method includes the steps of: transmitting an ultrasonic wave and receiving an ultrasonic reflected wave, which is produced by getting the ultrasonic wave reflected by a body tissue of an organism;

detecting the phase of the ultrasonic reflected wave; and calculating the magnitudes of positional displacement at a plurality of measuring points on the body tissue based on a signal obtained by the phase detecting step and also figuring out the greatest thickness difference between two of the measuring points and/or an elastic property based on the magnitudes of positional displacement. The step of calculating includes figuring out either the maximum and minimum thicknesses or thickness variations between the two points based on the magnitudes of positional displacement at the two points during a partial period of one cardiac cycle of the organism, and also calculating the greatest thickness difference and/or elastic property as the difference between the maximum and minimum values.

In one preferred embodiment, the body tissue is a circulatory organ, and the step of computing includes figuring out the elastic property based on a blood pressure value of the organism.

In this particular preferred embodiment, the partial period of the one cardiac cycle is set in sync with a biomedical signal obtained from the organism.

In a specific preferred embodiment, the biomedical signal is represented as an electrocardiogram by an electrocardiograph.

More specifically, the partial period of the one cardiac cycle is set based on at least one of P, Q, R, S, T and U waves of the electrocardiogram.

Alternatively, the partial period of the one cardiac cycle is set based on the R and T waves of the electrocardiogram.

In still another preferred embodiment, the biomedical signal is represented as a phonocardiogram by a phonocardiograph.

In this particular preferred embodiment, the partial period of the one cardiac cycle is set based on at least one of I, II, III and IV sounds of the phonocardiogram.

In yet another preferred embodiment, the biomedical signal is represented as a sphygmogram by a sphygmograph.

In this particular preferred embodiment, the partial period of the one cardiac cycle is set based on at least one of S, P, T, C and D waves of the sphygmogram.

In yet another preferred embodiment, the step of computing includes calculating in advance a positional displacement waveform, showing the magnitude of positional displacement of the body tissue during the one cardiac cycle, and setting the partial period of the one cardiac cycle based on the positional displacement waveform.

In yet another preferred embodiment, the step of computing includes calculating in advance a thickness variation waveform, showing a variation in the thickness of the body tissue during the one cardiac cycle, according to the magnitude of positional displacement and setting the partial period of the one cardiac cycle based on the thickness variation waveform.

In yet another preferred embodiment, the step of computing includes calculating in advance a vascular caliber variation waveform, showing a variation in the vascular caliber of the body tissue during the one cardiac cycle, according to the magnitude of positional displacement and setting the partial period of the one cardiac cycle based on the vascular caliber variation waveform.

In yet another preferred embodiment, the partial period of the one cardiac cycle includes at least a part, and sometimes all, of an ejection period.

In an alternative preferred embodiment, the partial period of the one cardiac cycle includes at least a part, and sometimes all, of a systolic phase.

In yet another preferred embodiment, the partial period accounts for 5% to 75% of the one cardiac cycle.

In yet another preferred embodiment, the method further includes the step of displaying the greatest thickness difference and/or elastic property. The step of computing includes calculating the greatest thickness difference and/or elastic property during the rest of the one cardiac cycle after the partial period has expired. And the step of displaying includes starting to display the greatest thickness difference and/or elastic property during the one cardiac cycle including the partial period.

In yet another preferred embodiment, the step of transmitting the ultrasonic wave and receiving the ultrasonic reflected wave is carried out during the partial period of the one cardiac cycle but stopped during the rest of the one cardiac cycle.

According to the present invention, the computing section figures out either the maximum and minimum thicknesses or the maximum and minimum thickness variations based on the magnitudes of positional displacement during a partial period of one cardiac cycle of an organism, and also figures out the elastic property using the maximum and minimum values obtained. As a result, the elastic property can be measured accurately with the influence of noise reduced.

Other features, elements, processes, steps, characteristics and advantages of the present invention will become more apparent from the following detailed description of preferred embodiments of the present invention with reference to the attached drawings.

Figure 5:
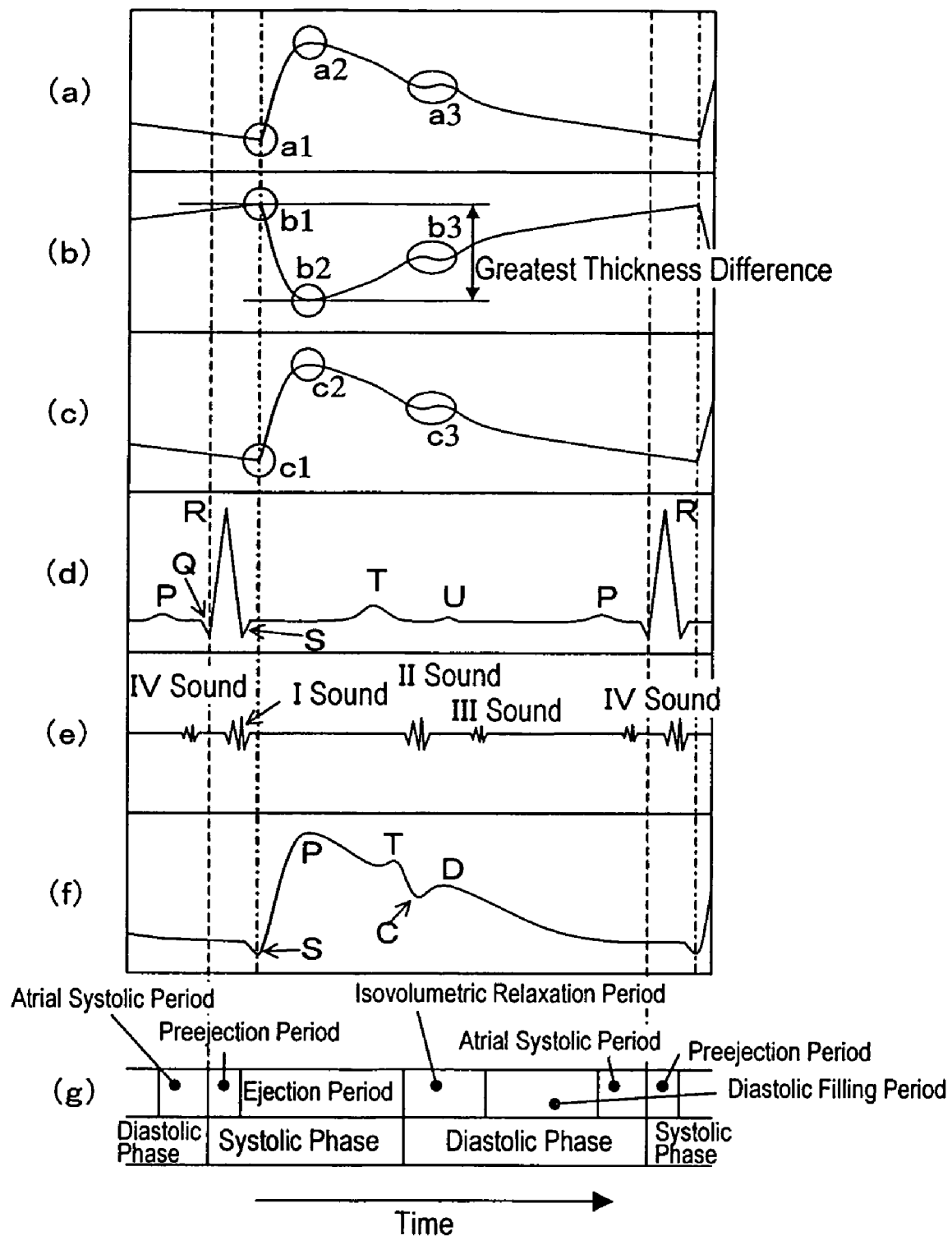

Portions (a), (b) and (c) of FIG. 5 are graphs showing the magnitude of positional displacement, variation in thickness and variation in the inside diameter of the blood vessel as measured on a human carotid artery by the ultrasonic diagnostic apparatus of the present invention; portions (d), (e) and (f) of FIG. 5 show an electrocardiogram, a phonocardiogram and a sphygmogram; and chart (g) of FIG. 5 shows phenomena occurring in one cardiac cycle.

Figure 6:
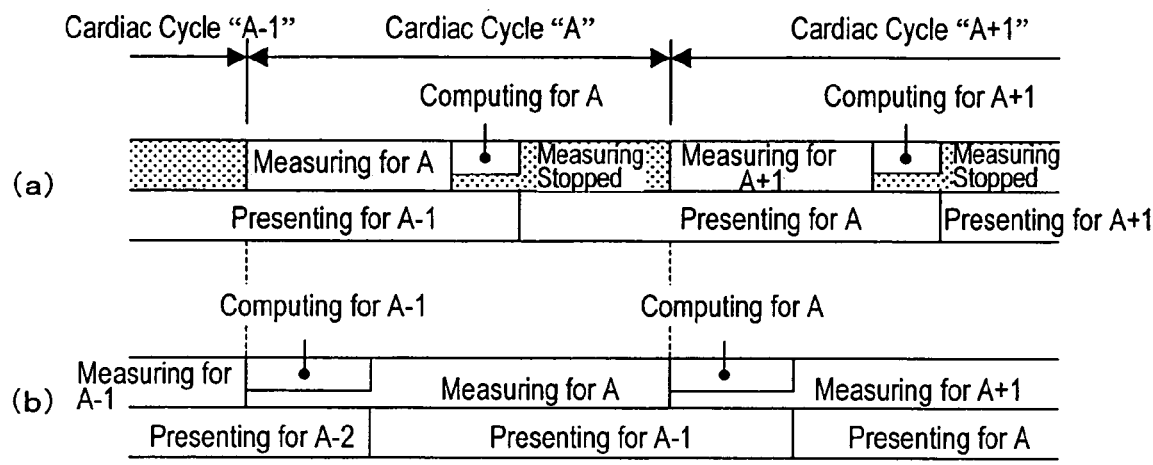

Chart (a) of FIG. 6 shows the timings of measuring, calculating and presenting by the ultrasonic diagnostic apparatus of the present invention, while chart (b) of FIG. 6 shows the timings of measuring, calculating and presenting by a conventional ultrasonic diagnostic apparatus.

Figure 7:
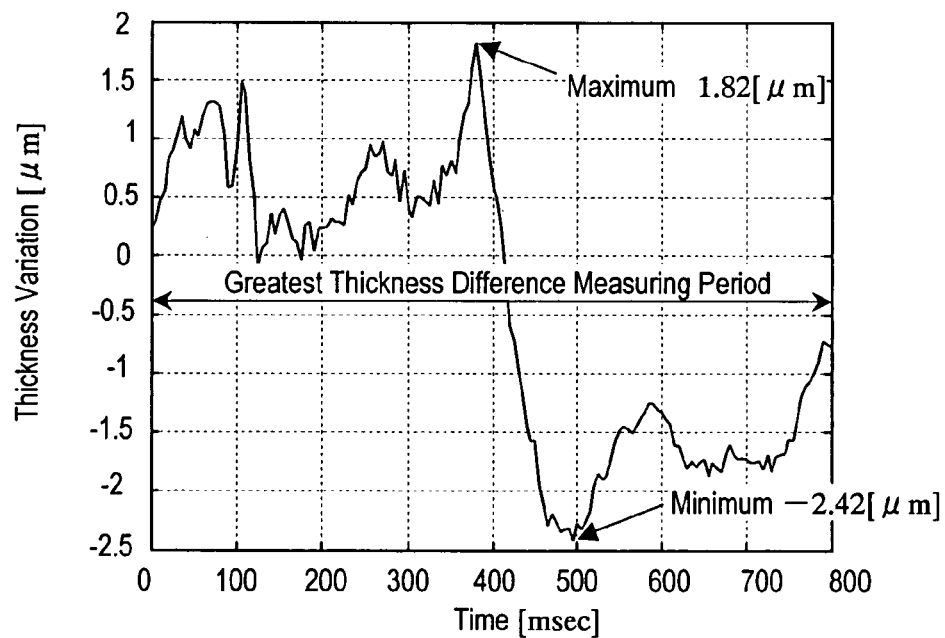

FIG. 7 is a graph showing a variation in the thickness of the rear wall of a human carotid artery with time.

FIG. 8 is a graph showing a variation in the thickness of the rear wall of a human carotid artery with time where the period for searching for the maximum and minimum thickness variations is set shorter than one cardiac cycle.

DETAILED DESCRIPTION OF PREFERRED EMBODIMENTS

An ultrasonic diagnostic apparatus according to the present invention estimates the motion velocity of each portion of an object under measurement and also figures out the greatest thickness difference and elastic property of each very small area. The ultrasonic diagnostic apparatus of the present invention can be used particularly effectively to evaluate the elastic property of each portion of an organism and also has sufficiently high spatial resolution. That is why the ultrasonic diagnostic apparatus of the present invention is preferably used to figure out the greatest thickness difference and elastic property of a vascular wall. Thus, an ultrasonic diagnostic apparatus according to a preferred embodiment of the present invention will be described as being applied to figuring out the greatest thickness difference and elastic property of a vascular wall.

Figure 1:
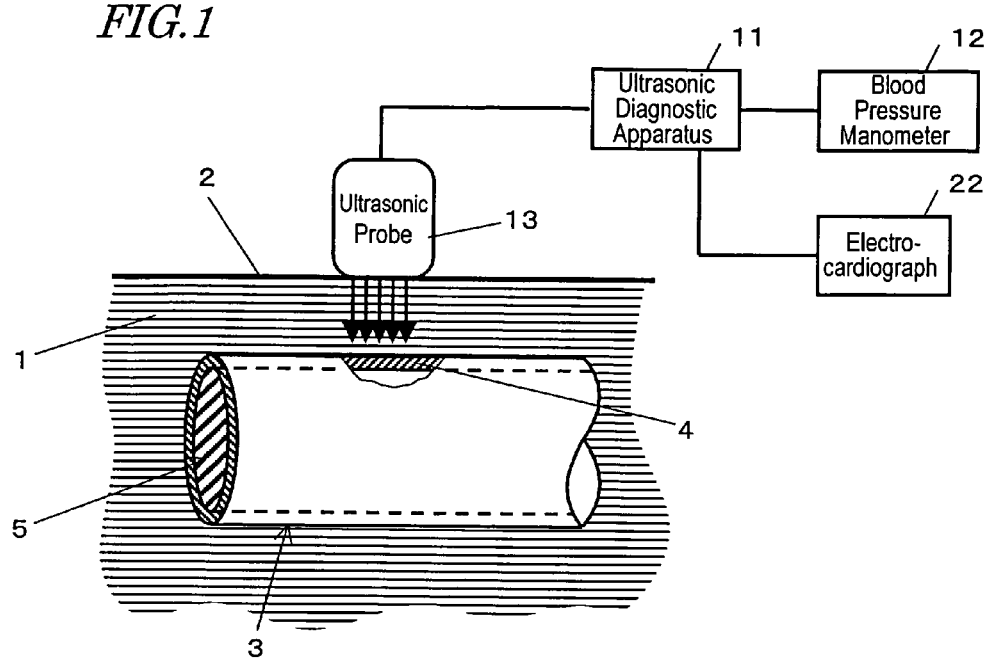
FIG. 1 is a block diagram showing an arrangement for a situation where an ultrasonic diagnostic apparatus according to the present invention is used to diagnose the tissue and attribute of a vascular wall.

FIG. 1 is a block diagram showing an arrangement for a situation where the ultrasonic diagnostic apparatus 11 of the present invention is used to diagnose the tissue and attribute of a vascular wall. An ultrasonic probe 13, connected to the ultrasonic diagnostic apparatus 11, is put in close contact with the body surface 2 of a person under measurement and transmits an ultrasonic wave into a body tissue including an extravascular tissue 1 and a blood vessel 3. The extravascular tissue 1 is made up of fats, muscles and so on. The transmitted ultrasonic wave is reflected by the blood vessel 3 and blood 5, scattered, and only a portion of it comes back to, and is received as an echo by, the ultrasonic probe 13. The ultrasonic probe 13 may be a known ultrasonic probe, which includes an array of ultrasonic vibrators (i.e., a group of ultrasonic vibrators) and which is used in a conventional ultrasonic diagnostic apparatus. The ultrasonic diagnostic apparatus 11 performs analysis and computations on a received signal, thereby acquiring the mobility information of the vascular wall 4. Also, a blood pressure manometer 12 is connected to the ultrasonic diagnostic apparatus 11 such that data about the blood pressure values of the person under measurement, collected by the blood pressure manometer 12, is input to the ultrasonic diagnostic apparatus 11.

In accordance with the method disclosed in Japanese Patent Application Laid-Open Publication No. 10-5226, the ultrasonic diagnostic apparatus 11 determines the instantaneous position of the object by a restricted minimum square method using both the amplitude and phase of a detection signal, thereby performing phase tracking highly accurately (where the magnitude of positional displacement has a measuring accuracy of about ±0.2 μm) and measuring variations in the position and thickness of a very small spot on the vascular wall 4 with time. In addition, by using blood pressure data obtained with the blood pressure manometer 12, the ultrasonic diagnostic apparatus 11 can also evaluate the elastic property of a very small spot on the vascular wall 4.

An electrocardiograph 22 is connected to the ultrasonic diagnostic apparatus 11, which receives an electrocardiogram from the electrocardiograph 22 and uses it as a trigger signal that determines the timings of data acquisition and data resetting. More particularly, the ultrasonic diagnostic apparatus 11 sets a partial period of one cardiac cycle of the organism using the electrocardiogram and evaluates the elastic property according to only the information collected during the designated partial period. In this manner, the influence of noise can be reduced and the elastic property can be evaluated highly accurately.

Figure 2:
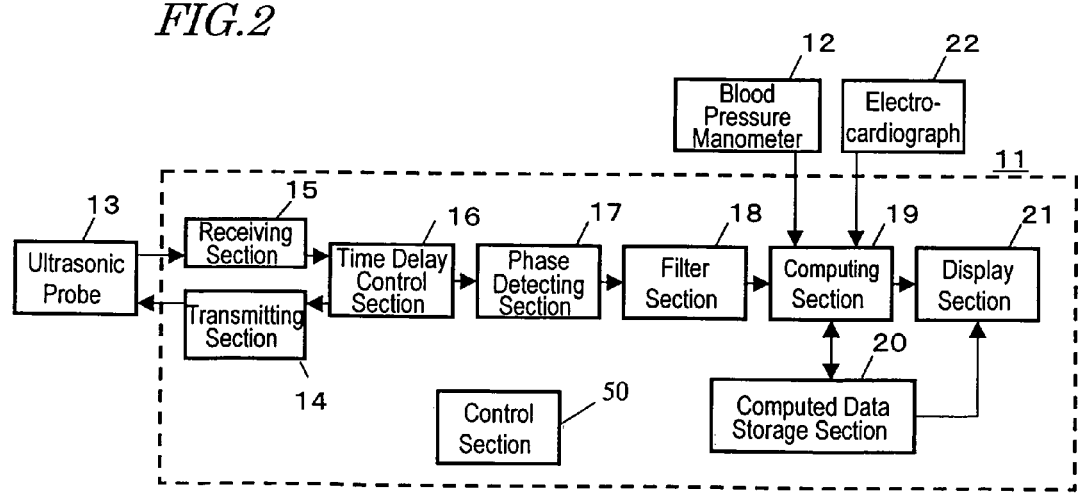
FIG. 2 is a block diagram showing a configuration for the ultrasonic diagnostic apparatus of the present invention.

Hereinafter, the configuration and operation of the ultrasonic diagnostic apparatus 11 will be described in detail. FIG. 2 is a block diagram showing a configuration for the ultrasonic diagnostic apparatus 11. The ultrasonic diagnostic apparatus 11 includes a transmitting section 14, a receiving section 15, a time delay control section 16, a phase detecting section 17, a filter 18, a computing section 19, a computed data storage section 20, and a display section 21. The ultrasonic diagnostic apparatus 11 further includes a control section 50 (implemented as a computer, for example) for performing an overall control on all of these sections.

The transmitting section 14 generates a predetermined drive pulse signal and outputs it to the ultrasonic probe 13. An ultrasonic transmitted wave, transmitted by the ultrasonic probe 13 in response to the drive pulse signal, is reflected and scattered by a body tissue such as the vascular wall 4 to produce an ultrasonic reflected wave, which is then received at the ultrasonic probe 13.

The receiving section 15 receives the ultrasonic reflected wave through the ultrasonic probe 13, and includes an A/D converting section for amplifying the ultrasonic reflected wave and then converting the amplified wave into a digital signal. The transmitting section 14 and receiving section 15 may be made of electronic components, for example.

The time delay control section 16 is connected to the transmitting section 14 and receiving section 15 in order to control the time delay of the drive pulse signal to be supplied from the transmitting section 14 to a group of ultrasonic vibrators in the ultrasonic probe 13. In this manner, an ultrasonic beam of the ultrasonic transmitted wave to be transmitted from the ultrasonic probe 13 can have its acoustic line direction and depth of focus changed. Also, by controlling the time delay of a received reflected wave signal that has been received by the ultrasonic probe 13 and then amplified by the receiving section 15, the acoustic line direction of the ultrasonic wave to receive can be changed. The output of the time delay control section 16 is passed to the phase detecting section 17.

The phase detecting section 17 detects the phase of the received reflected wave signal, of which the time delay has been controlled by the time delay control section 16, thereby splitting the signal into a real part signal and an imaginary part signal, which are then input to the filter section 18. The filter section 18 filters out components that have not been reflected by the object of measurement and other noise components. The phase detecting section 17 and filter section 18 may be implemented as either a software program or hardware components.

The computing section 19 calculates the motion velocities at a plurality of tracking points that have been set inside of the vascular wall 4 by using the real part and imaginary part signals of the phase-detected signal and then integrates these motion velocities together, thereby figuring out the magnitudes of displacement with time at the respective tracking points inside of the vascular wall 4. Then, the computing section 19 selectively calculates the difference in the magnitude of positional displacement between two arbitrary points among those magnitudes of positional displacement, thereby obtaining the difference in thickness between those two points. Furthermore, based on the greatest thickness difference obtained as the difference between the maximum and minimum thickness variations thus calculated and on the blood pressure data collected with the blood pressure manometer 12, the computing section 19 can evaluate the elastic property of the tissue located between the two points. The electrocardiogram obtained by the electrocardiograph 22 is input to the computing section 19 and used as a trigger signal for determining the timings of data acquisition and data resetting. For this purpose, the electrocardiograph 22 may be replaced with any other biomedical signal detecting means such as a phonocardiograph or a sphygmograph. In that case, a phonocardiogram or a sphygmogram may be used as a trigger signal instead of the electrocardiogram.

Data about the magnitudes of positional displacement, variations in thickness, and elastic property that have been figured out by the computing section 19 may be stored in, and readily read out from, the computed data storage section 20, and may also be input to the display section 21 so as to be visualized into a two-dimensional image. Furthermore, if the display section 21 is connected to the computed data storage section 20, those various data stored may also be presented on the display section 21 when required. Those data computed by the computing section 19 are preferably output to both the display section 21 and the storage section 20 so as to be presented in real time and saved for future use at the same time. However, one of the display section 21 and the storage section 20 may be omitted as well.

Figure 3:
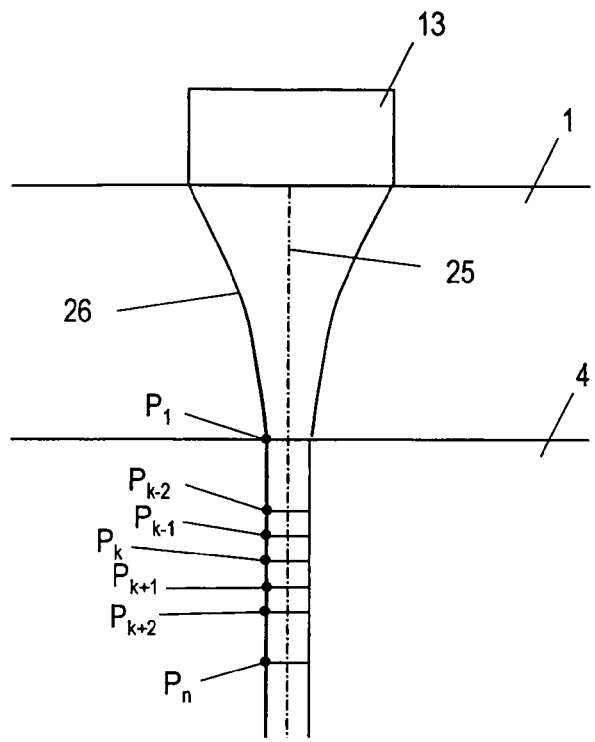
FIG. 3 schematically illustrates an ultrasonic beam propagating through a body tissue.

Next, it will be described in detail with reference to FIG. 3 how to calculate the magnitude of positional displacement of a body tissue. As shown in FIG. 3, an ultrasonic transmitted wave, emitted from the ultrasonic probe 13, propagates as an ultrasonic beam 26 with a certain finite width through the extravascular tissue 1 and vascular wall 4. In the meantime, a portion of the ultrasonic wave is either reflected or scattered by the extravascular tissue 1 or the vascular wall 4 back toward the ultrasonic probe 13 and received there as an ultrasonic reflected wave. The ultrasonic reflected wave is detected as a time series signal r(t). The closer to the ultrasonic probe 13 a portion of the tissue that has reflected the ultrasonic wave to produce the time series signal, the closer to the origin the signal is located on the time axis. The width (i.e., beam spot size) of the ultrasonic beam 26 can be controlled by changing the time delay.

As described above, the ultrasonic reflected wave may be produced by both the extravascular tissue 1 and the vascular wall 4. However, since the vascular wall tissue is the object of measurement in this preferred embodiment, the following description will be focused on only the reflection from the vascular wall 4. A plurality of measuring points $P_n$, which are located on an acoustic line 25 (i.e., the center axis of the ultrasonic beam) in the vascular wall 4, are arranged at regular intervals in the order of $P_1, P_2, P_3, \ldots, P_k, \ldots$ and $P_n$ (where n is natural number that is equal to or greater than three) where $P_1$ is a located closest to the ultrasonic probe 13. Supposing the coordinates that are defined in the depth direction with respect to the surface of the extravascular tissue 1 as the origin are represented by $Z_1, Z_2, Z_3, \ldots, Z_k, \ldots$ and $Z_n$, an ultrasonic wave reflected from a measuring point $P_k$ is located at $t_k=2Z_k/C$ on the time axis, where c is the velocity of the ultrasonic wave in the body tissue. The reflected wave signal r(t) has its phase detected by the phase detecting section 17 and the phase-detected signal is split into a real part signal and an imaginary part signal, which are then passed through the filter section 18. Under the restriction that the amplitude does not change, but only the phase and reflection spot change, between the reflected wave signal r(t) and another reflected wave signal r(t+Δt) obtained after a very small amount of time Δt, the computing section 19 calculates the phase difference by a minimum square method so as to minimize the waveform mismatch between the reflected wave signals r(t) and r(t+Δt). That is to say, the computing section 19 adopts a restricted minimum square method. The motion velocity $V_n(t)$ of the measuring point $P_n$ is derived from this phase difference and then integrated, thereby obtaining the magnitude of positional displacement $d_n(t)$.

Figure 4:
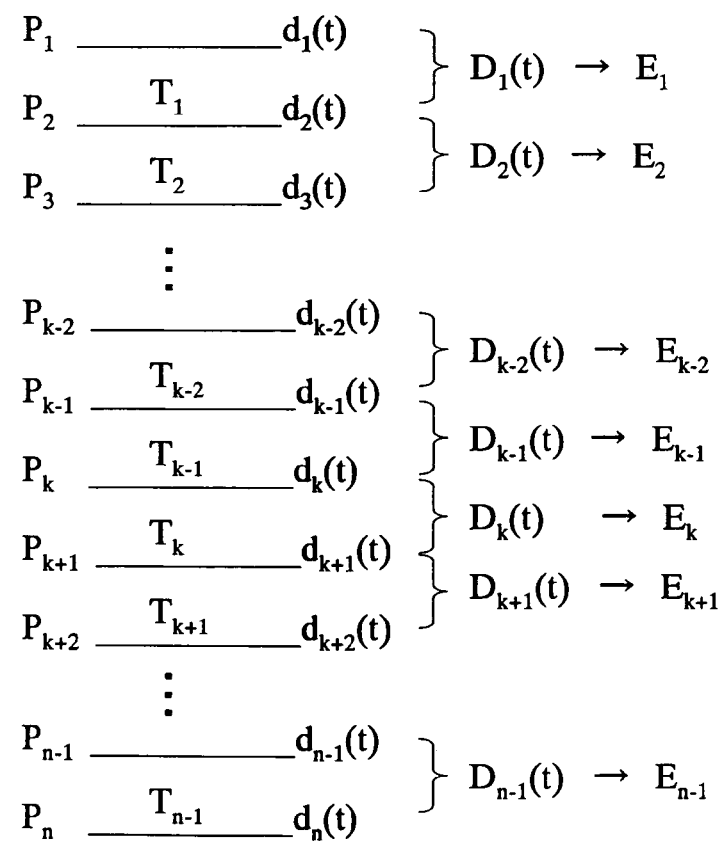
FIG. 4 shows the relationship between the measuring point and the elasticity at the measuring point.

FIG. 4 shows the relationship between the measuring point $P_n$ and the tissue under measurement $T_n$, of which the elasticity needs to be calculated. A tissue under measurement $T_k$ is located between two adjacent measuring points $P_k$ and $P_{k+1}$ so as to have a thickness h. That is to say, a number (n−1) of tissues under measurement $T_1$ through $T_{n-1}$ can be sampled from a number n of measuring points $P_1$ through $P_n$.

The variation $D_k(t)$ in the thickness of the tissue under measurement $T_k$ (i.e., the magnitude of its stretch or shrinkage) is obtained as the difference between the magnitudes of positional displacement $d_k(t)$ and $d_{k+1}(t)$ of the measuring points $P_k$ and $P_{k+1}$ (i.e., $D_k(t)=d_{k+1}(t)-d_k(t)$). The thickness of the tissue $T_k$ of the vascular wall 4 varies when the blood flowing through the blood vessel, made up of the vascular wall 4, changes with the cardiac cycle. Accordingly, the elasticity $E_k$ (i.e., the strain rate) of the tissue under measurement $T_k$ in the vascular radial direction is given by:

$$E_k=(\Delta p \times H_k)/\Delta h_k$$

where $H_k$ is the maximum thickness of the tissue under measurement $T_k$ (i.e., the value associated with the lowest blood pressure), $\Delta h_k$ is the difference between the maximum and minimum variations $D_k(t)$ in the thickness of the tissue under measurement, and $\Delta p$ is pulse pressure that is the difference between the lowest and highest blood pressures.

In the example described above, the elasticity is calculated between two adjacent measuring points. However, the elasticity may also be calculated between two arbitrary ones of the multiple measuring points. In that case, the elasticity can be calculated in a similar manner by using the maximum thickness and the maximum and minimum thickness variations between the two points selected.

If the tissue under measurement is a circulatory organ such as a vascular wall, then the greatest thickness difference Δh, pulse pressure Δp and maximum thickness H are all updated every cardiac cycle. That is why the elastic property is preferably evaluated in sync with every cardiac cycle. To calculate the greatest thickness difference Δh in one cardiac cycle, the maximum and minimum thickness variations in one cardiac cycle need to be obtained. According to the present invention, these maximum and minimum thickness variations are searched for in a period that is shorter than one cardiac cycle. Hereinafter, the timings of measuring these numerical values will be described in detail. Portions (a), (b) and (c) of FIG. 5 respectively show the magnitude of positional displacement, variation in thickness, and variation in the inside diameter of the blood vessel as measured by the ultrasonic diagnostic apparatus 11 at an arbitrary point on the vascular wall of a human carotid artery. On the other hand, portions (d), (e) and (f) of FIG. 5 respectively show the electrocardiogram, phonocardiogram and sphygmogram, which are biomedical signals obtained by measuring the displacements shown in portions (a), (b) and (a) of FIG. 5. In all of these portions (a) through (f) of FIG. 5, the abscissa represents the time. That is to say, these portions share the same time axis in common. Meanwhile, the chart (g) of FIG. 5 shows the cardiac cycle phenomena on the time axis of portions (a) through (f).

As shown in the chart (g) of FIG. 5, one cardiac cycle is roughly divided into a systolic phase and a diastolic phase. The systolic phase is subdivided into a preejection period and an ejection period and the diastolic phase is subdivided into an isovolumetric relaxation period, a diastolic filling period and an atrial systolic period. The systolic phase substantially corresponds to a range that starts with the beginning of Q wave and terminates with the end of T wave on the electrocardiogram (i.e., portion (d) of FIG. 5) and to a range that starts with the beginning of I sound and terminates with the end of II sound on the phonocardiogram (i.e., portion (e) of FIG. 5). On the other hand, the diastolic phase substantially corresponds to a range that starts with the end of T wave and terminates with the beginning of Q wave on the electrocardiogram and to a range that starts with the beginning of II sound and terminates with the beginning of I sound on the phonocardiogram. In FIG. 5, one cardiac cycle, which is triggered by the beginning of a systolic phase as observed in a heart, is indicated by the dashed lines.

The magnitude of positional displacement, variation in thickness and variation in the inside diameter of the blood vessel shown in portions (a), (b) and (c) of FIG. 5 and the sphygmogram shown in portion (f) if FIG. 5 are measured at the carotid artery, which is located away from the heart. That is why when about 0.1 second has passed after various events of one cardiac cycle have occurred in the heart, phenomena corresponding to these events of the heart are observed on these magnitudes of displacement and a sphygmogram. For example, the systolic phase of the sphygmogram (see portion (f) of FIG. 5) starts with S wave but its timing trails by about 0.1 second behind the beginning of the systolic phase as indicated by the dashed line. In FIG. 5, one cardiac cycle, which is triggered by the beginning of a systolic phase as observed in the carotid artery, is indicated by the one dot chain.

When blood is ejected from the heart, the sphygmogram curve rises steeply from S wave into P wave. After having reached the peak of the P wave, the sphygmogram curve makes a small upward hump of T wave, makes a notch of C wave, makes another small upward hump of D wave, and then falls gently. The C and D waves are called "dichrotic notch" and "dichrotic wave", respectively, and are events brought about by the closure of the aortic valve. In the variation in the thickness of the carotid artery shown in portion (b) of FIG. 5, the maximum value b1 is encountered at the same time as the S wave of the sphygmogram, while the minimum value b2 is found at the same time as the P wave of the sphygmogram. That is to say, it can be seen that the greatest thickness difference $\Delta h$ does not have to be calculated in the overall cardiac cycle but in just a period in which the S and P waves of the sphygmogram are monitored. Likewise, the maximum and minimum blood pressures for calculating the pulse pressure $\Delta p$ can also be obtained from these S and P waves. Furthermore, the maximum thickness H can be obtained when the thickness variation reaches its maximum value b1.

Consequently, the elastic property of a circulatory organ such as the vascular wall of an organism can be measured in either a period including the ejection period and the ventricular systolic period (during which the S and P waves of the sphygmogram are observed) in one cardiac cycle or a period including at least a part of the ejection period and at least a part of the ventricular systolic period. Stated otherwise, no maximum or minimum thickness variation is present within the diastolic phase of one cardiac cycle. Accordingly, even if measurements were done in this phase to search for the maximum and minimum values, no desired maximum and minimum values should be obtained.

According to the present invention, by taking advantage of such a tendency of the thickness variation, the period for obtaining properly the maximum and minimum thickness variations within one cardiac cycle is set shorter than one cardiac cycle. By adopting such a shortened measuring time, the chances to recognize noise as the maximum or minimum value in error can be reduced. For example, if the measurements are done only within the ejection period of one cardiac cycle, then the chances to be affected by noise can be reduced to less than one third because the ejection period accounts for approximately 30% of one cardiac cycle. In addition, by shortening the measuring time, the computational complexity of the measurements can also be reduced. As a result, the manufacturing cost of the ultrasonic diagnostic apparatus can be cut down because there is no need to build a lot of memories in the ultrasonic diagnostic apparatus or to use any high-performance computer with high processing capabilities. Or an ultrasonic diagnostic apparatus that can get measurements done at high speed is realized.

On top of that, the thickness difference and elastic property calculated can be presented on the display section 21 even before one cardiac cycle is completed. Chart (a) of FIG. 6 shows the timings of measuring, calculating and presenting by the ultrasonic diagnostic apparatus of the present invention, while chart (b) of FIG. 6 shows the timings of measuring, calculating and presenting by a conventional ultrasonic diagnostic apparatus. As shown in the chart (a) of FIG. 6, the measuring period is a partial period of (i.e., shorter than) one cardiac cycle around an arbitrary cardiac cycle A. The partial period may be from R wave through T wave of the electrocardiogram shown in portion (d) of FIG. 5. As soon as the cardiac cycle A begins, the computing section 19 measures the magnitude of positional displacement and the variation in thickness. In the meantime, the display section 21 is presenting the results of the previous cardiac cycle A−1. On getting the measurements done in the predetermined partial period, the computing section 19 starts computation processing based on the results of measurements. More specifically, the computing section 19 extracts the maximum and minimum thickness variations, for example. Then, the elastic property calculated for the cardiac cycle A is presented on the display section 21.

At this point in time, the cardiac cycle of the person under measurement is still "A". That is to say, the display section 21 starts to present the elastic property for the cardiac cycle A during the cardiac cycle A. Thus, the operator of the ultrasonic diagnostic apparatus 11 can check the results of computations for the cardiac cycle A in real time and can use them in measurements for the next cardiac cycle A+1. More specifically, the operator can finely adjust the location of the ultrasonic probe 13 or release the ultrasonic probe 13 once and then hold it again more firmly. As shown in the chart (a) of FIG. 6, by making the transmitting section 14 stop driving the ultrasonic probe 13 after the measurements have been done for the cardiac cycle A, the ultrasonic diagnostic apparatus 11 can stop the measurements. By stopping the measurements, the load on a computer for controlling the ultrasonic diagnostic apparatus 11 can be lightened and the computations based on the results of measurements for the cardiac cycle A can be processed faster. As a result, the elastic property for the cardiac cycle A can be figured out more quickly.

When the computation processing for the cardiac cycle A is finished, the computing section 19 stops computing until the next cardiac cycle A+1 begins. Optionally, the computing section 19 may carry out any other type of signal processing (e.g., calculating the average of elastic properties at a number of most recent cardiac cycles) in this interval.

On the other hand, the conventional ultrasonic diagnostic apparatus as disclosed in Japanese Patent Application Laid-Open Publication No. 2000-229078, for example, carries out measurements throughout each cardiac cycle and then calculates the maximum and minimum thickness variations, the greatest thickness difference, and elastic property based on the measured values obtained as shown in chart (b) of FIG. 6. And these computations are done during the next cardiac cycle. More specifically, the conventional ultrasonic diagnostic apparatus carries out measurements during the cardiac cycle A and computations on the results of measurements during the next cardiac cycle A+1 as shown in the chart (b) of FIG. 6. In this case, the computation processing for the cardiac cycle A needs to be carried out in parallel with the measurements for the cardiac cycle A+1. As a result, a heavy load is placed on the computer for controlling the ultrasonic diagnostic apparatus and it takes a lot of time to get the computation processing for the cardiac cycle A done. In addition, the measured values obtained through the entire cardiac cycle need to be processed and the degree of computational complexity is rather high, thus making the computation processing for the cardiac cycle A even longer. As a result, the computations cannot be done and the elastic property figured out for the cardiac cycle A cannot be presented on the display section 21 until some time after the cardiac cycle A+1 has begun. In this manner, a time lag is inevitable in the prior art before the results of measurements are presented. Consequently, it is difficult for the operator of the conventional ultrasonic diagnostic apparatus to finely adjust the location of the ultrasonic probe 13 or release the probe 13 once and then hold it again more firmly while watching the results presented on the display section 21.

It should be noted that Japanese Patent Application Laid-Open Publication No. 2000-229078 discloses a technique of analyzing a big amplitude displacement/motion of a vascular wall under a restriction that the sum of displacements at one impulse becomes equal to zero in order to measure a very small motion of the blood vessel with stability and accuracy. According to Japanese Patent Application Laid-Open Publication No. 2000-229078, the displacement/motion and variation in thickness need to be measured continuously all through one cardiac cycle. Japanese Patent Application Laid-Open Publication No. 2000-229078 also discloses a technique of calculating the average elasticity E of the blood vessel based on the ratio of the pulse pressure (i.e., the difference between the highest and lowest blood pressures ps and pd) to the maximum strain $\Delta \epsilon$ max. However, Japanese Patent Application Laid-Open Publication No. 2000-229078 does not mention at all the timings of obtaining the highest and lowest blood pressures ps and pd or the timings of obtaining the maximum and minimum thicknesses for calculating the maximum strain $\Delta \epsilon$ max. Consequently, Japanese Patent Application Laid-Open Publication No. 2000-229078 neither suggested nor taught calculating the maximum and minimum thickness variations in a partial period of one cardiac cycle.

Hereinafter, it will be described in further detail how to define a data acquisition period using a signal obtained by the biomedical signal detecting section.

As is clear from the respective graphs of FIG. 5, the times when the S and P waves of the sphygmogram are monitored and the times when the maximum and minimum thickness variations b1 and b2 are obtained can be set easily by using the biomedical signal. For example, if the electrocardiograph 22 is used as a biomedical signal detecting section as shown in portion (d) of FIG. 5, then the data acquisition period may be defined to last from R wave through T wave. That is to say, by regarding the R wave as a reference for starting the data acquisition period and the T wave as a reference for ending the data acquisition period, the maximum and minimum thickness variations can be obtained effectively. Optionally, the R wave may be replaced with P wave, Q wave or S wave, or the data acquisition period may be defined to last 0.5 second from the R wave or to last a period of time accounting for 40% of one cardiac cycle from the R wave. Even so, similar effects are also achieved.

Alternatively, if a phonocardiograph is used as a biomedical signal detecting section as shown in portion (e) of FIG. 5, then the data acquisition period may be defined so as to last from I sound through II sound to obtain the maximum and minimum thickness variations effectively. Optionally, the I sound may be replaced with IV sound or the II sound may be replaced with III sound. Alternatively, the data acquisition period may be defined to last 0.5 second from the I sound or to start earlier than the I sound by a period of time accounting for 10% of one cardiac cycle and to end later than the I sound by a period of time accounting for 30% of one cardiac cycle.

As another alternative, if a sphygmograph is used as a biomedical signal detecting section as shown in portion (f) of FIG. 5, then the data acquisition period may be defined so as to last from S wave through C wave to obtain the maximum and minimum thickness variations effectively. Optionally, the C wave may be replaced with T wave or D wave. Alternatively, the data acquisition period may be defined to last 0.5 second from the S wave or to start earlier than the S wave by a period of time corresponding to 10% of one cardiac cycle and to end later than the S wave by a period of time corresponding to 30% of one cardiac cycle.

Furthermore, instead of providing a separate instrument for detecting the biomedical signal outside of the ultrasonic diagnostic apparatus 11, the numerical values measured by the ultrasonic diagnostic apparatus 11 may also be used as a trigger signal. As shown in portion (a) of FIG. 5, there are local maximum and minimum points such as the points a1, a2 and a3, where the magnitude of positional displacement changes uniquely, in the curve representing the magnitudes of positional displacement at arbitrary points on the carotid artery under measurement. That is why even if those points a1, a2 and a3 are extracted by the computing section 19, the period for obtaining the maximum and minimum thickness variations can also be defined within one cardiac cycle. It should be noted that the point a1 is an event resulting from a point with the lowest blood pressure at the measuring point on the blood vessel 3, the point a2 is an event resulting from a point with the highest blood pressure at the measuring point on the blood vessel 3, and the point a3 is an event resulting from a dichrotic notch.

If the measuring period is defined based on the magnitudes of positional displacement, the maximum and minimum thickness variations can be easily obtained by setting the data acquisition period from the point a1 through the point a3, for example. Alternatively, the point a3 may be replaced with the point a2. As another alternative, the data acquisition period may also be defined to last 0.5 second from the point a1 or to begin earlier than a1 by an amount of time corresponding to 10% of one cardiac cycle and end later than a2 by the same amount of time.

Optionally, as shown in portion (c) of FIG. 5, the points c1, c2 and c3 may be extracted from the curve representing the variation in the inside diameter of the blood vessel and used for defining the measuring period. Or the points b1, b2 and b3 may be extracted from the curve representing the thickness variation shown in portion (b) of FIG. 5 and used for setting the measuring period.

To define the period for deriving the maximum and minimum thickness variations by using the biomedical signal generated by the biomedical signal detecting section, the electrocardiogram obtained by the electrocardiograph 22 may be input to the computing section 19 as shown in FIGS. 1 and 2. If the R wave is detected, the thickness variation may be calculated. But if the T wave is detected, then the calculation may be stopped as described above. The R and T waves may be detected by making the computing section 19 use the amplitude of the electrocardiogram, values obtained by differentiating the electrocardiogram, and their timings of appearance. Alternatively, the electrocardiograph 22 may also detect the R and T waves and may output a control signal to the computing section 19 on detecting those waves.

Also, if the timing of a specific signal such as a waveform that triggers the biomedical signal is close to the timing at which the maximum or minimum thickness variation is obtained or if a specific signal that rises after the maximum or minimum thickness variation is reached is used as a trigger, then the signal may be used as a trigger in the measuring period of the next cardiac cycle that follows the period in which the specific signal was obtained as a trigger.

Considering the individual differences among persons under measurement, the measuring period for obtaining the maximum and minimum thickness variations preferably has a length corresponding to 5% through 75% of one cardiac cycle. The reasons are as follows. Specifically, if the measuring period were shorter than 5% of one cardiac cycle, then at least one of the maximum and minimum thickness variations could not be obtained. However, if the measuring period were longer than 75% of one cardiac cycle, then the effects to be achieved by shortening the measuring period could not be achieved fully and the measurement could be subjected to noise more easily. For these reasons, the measuring period, defined by using the biomedical signal as a trigger, preferably falls within this range. By setting the measuring period within this range, the computational complexity and the influence of noise would be reduced by approximately 25% to 95%.

As described above, the variation in thickness is obtained as a difference in the magnitude of positional displacement between two points defining the thickness. Accordingly, the maximum and minimum thickness variations may be derived from the magnitudes of positional displacement between two points during the period in which the maximum and minimum thickness variations should be obtained. The ultrasonic diagnostic apparatus 11 may obtain the maximum and minimum thickness variations by measuring the magnitudes of positional displacement all through one cardiac cycle (i.e., continuously) and extracting some of the magnitudes of positional displacement that fall within the period for obtaining the maximum and minimum thickness variations. Alternatively, the ultrasonic diagnostic apparatus 11 may also obtain the maximum and minimum thickness variations by measuring the magnitudes of positional displacement only within the particular period of one cardiac cycle (i.e., intermittently). The maximum and minimum thickness variations may be calculated either in real time during that period defined by the biomedical signal, for example, or during some period that does not agree with that period. To reduce the load on the computer for controlling the overall ultrasonic diagnostic apparatus 11 and shorten the amount of time it takes to get the calculations done by the computing section, the magnitudes of positional displacement are preferably measured intermittently.

Also, while diagnosed by the ultrasonic diagnostic apparatus, the organism is laid to rest and is likely to have little variation in cardiac rate. That is why the measuring period does not have to be defined every cardiac cycle. Alternatively, once defined in accordance with the biomedical information described above, the measuring period may be repeated at the same intervals a number of times. Meanwhile, if the biomedical signal is detected every cardiac cycle and if the measuring period is defined based on that biomedical signal, then the elastic property can be evaluated just as intended even when the organism has an irregular cardiac cycle due to arrhythmia, for example.

In the preferred embodiment described above, the measuring period is supposed to be set with the specific signal obtained by only one type of biomedical signal detecting section. Optionally, the measuring period may also be defined by specific signal obtained by a plurality of biomedical signal detecting sections. For example, the R wave of the electrocardiogram may be used as a signal that defines the beginning of a measuring period and the point c3 of the variation in the inside diameter of the blood vessel may be used as a signal that defines the end of the measuring period.

Also, in the preferred embodiment described above, the greatest thickness difference is obtained by finding the maximum and minimum thickness variations. Alternatively, the thicknesses themselves may be measured and the greatest thickness difference may be obtained from the maximum and minimum thicknesses. Suppose the thickness variation is already known. In that case, if the thickness when the thickness variation starts to be measured is known, then the variation in thickness with time can be obtained as the sum of the thickness at the start of measuring and the thickness variation. The thickness at the start of measuring is nothing but the initial value of the distance between two arbitrary points to calculate the magnitudes of positional displacement for, and is a known parameter for the ultrasonic diagnostic apparatus 11 of this preferred embodiment.

Furthermore, a waveform to be a trigger signal for setting the measuring period may be presented on the display section 21 and the measuring period may be highlighted on that waveform. Then the operator of the apparatus can easily check out the period for obtaining the maximum and minimum thicknesses or the maximum and minimum thickness variations. If the measuring period presented is different from the desired measuring period, the operator may modify the measuring period into the desired one either by manually finely adjusting the measuring period or by changing the source of the trigger signal.

The greatest thickness difference and elastic property of a portion of a carotid wall were measured with this ultrasonic diagnostic apparatus 11. The results are as follows.

FIG. 7 shows the variation in the thickness of the rear wall of a human carotid artery, which was measured with the ultrasonic diagnostic apparatus 11. The person under measurement was a 41-year-old man and the variation was measured for one cardiac cycle (of about 800 ms) using the R wave of his electrocardiogram as a trigger signal. In FIG. 7, the greatest thickness difference in one cardiac cycle was 1.82+2.42=4.24 µm. In this case, the maximum thickness at the measuring point was 160 µm and the person under measurement had a blood pressure difference of 40 mmHg (=5.33 kPa). Consequently, the elastic property E was 5.33× 160/4.24 =201 kPa.

However, these maximum and minimum values were respectively obtained at about 380 ms and at about 500 ms in one cardiac cycle as shown in FIG. 7. As can be seen clearly if the results shown in FIG. 7 are compared with portion (b) of FIG. 6, the thickness difference resulting in these maximum and minimum values is an impossible behavior as a variation in the thickness of a vascular wall and is believed to have been caused by noise. In this manner, when the maximum and minimum thickness variations are obtained all through one cardiac cycle, those values may sometimes be affected by noise and inaccurate elastic property may be obtained.

FIG. 8 shows the variation in the thickness of the rear wall of the same human carotid artery as that of FIG. 7. As shown in FIG. 8, if the period for obtaining the maximum and minimum thickness variations is changed to last 300 ms from the R wave trigger signal, then correct maximum and minimum values can be selected. In that case, the greatest thickness difference was 1.50+0.11=1.61 µm. The maximum thickness at the measuring point was 160 µm and the person under measurement had a blood pressure difference of 5.33 kPa. Consequently, the elastic property E was 5.33×160/1.61=530 kPa.

By changing the measuring period, the data acquisition period can be shortened to about three-eighths, and therefore, the memory for storing the data acquired can have smaller capacity and the computer needs to do computations of reduced complexity per cardiac cycle. Consequently, the memory to be built in the ultrasonic diagnostic apparatus can have a reduced capacity and the elastic property can be evaluated faster. Optionally, a computer with low computation performance may also be adopted since the computational complexity has been reduced. Then, the cost of the ultrasonic diagnostic apparatus can be cut down.

As described above, the ultrasonic diagnostic apparatus of the present invention calculates the maximum and minimum thickness variations based on the magnitude of positional displacement in a period that is shorter than one cardiac cycle. Thus, the apparatus can obtain more accurate measuring results with the influence of noise minimized.

The ultrasonic diagnostic apparatus of the present invention can be used effectively to evaluate the elastic property of a vital tissue. Among other things, the apparatus can be used particularly effectively to detect or prevent the disease of arterial sclerosis by measuring the elastic property of a vascular wall.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

This application is based on Japanese Patent Application No. 2004-151689 filed May 21, 2004, the entire contents of which are hereby incorporated by reference.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An ultrasonic diagnostic apparatus comprising:
   a transmitting section for driving an ultrasonic probe that sends out an ultrasonic transmitted wave toward a body tissue of an organism;
   a receiving section for receiving an ultrasonic reflected wave through the ultrasonic probe, the ultrasonic reflected wave being produced by getting the ultrasonic transmitted wave reflected by the body tissue;
   a phase detecting section for detecting the phase of the ultrasonic reflected wave; and
   a computing section for calculating the magnitudes of positional displacement at a plurality of measuring points inside the body tissue, wherein each measuring point is spaced apart in a depth direction with respect to a surface of the body tissue relative to each other measuring point, based on a signal obtained by the phase detecting section and also figuring out an elastic property between two of the measuring points based on the magnitudes of positional displacement,
   wherein the body tissue is a circulatory organ,
   wherein the computing section figures out the maximum and minimum values of thicknesses or thickness variations between the two points based on the magnitudes of positional displacement at the two points during a measuring period set as a predetermined partial period shorter than one cardiac cycle of the organism, calculates a greatest thickness difference between the maximum and minimum thickness or thickness variations, receives information about a blood pressure value of the organism and also calculates the elastic property based on the greatest thickness difference and the blood pressure value, and
   wherein the partial period of the one cardiac cycle is set in sync with a biomedical signal obtained from the organism.

2. The ultrasonic diagnostic apparatus of claim 1, wherein the biomedical signal is represented as an electrocardiogram by an electrocardiograph.

3. The ultrasonic diagnostic apparatus of claim 2, wherein the partial period of the one cardiac cycle is set based on at least one of P, Q, R, S, T and U waves of the electrocardiogram.

4. The ultrasonic diagnostic apparatus of claim 2, wherein the partial period of the one cardiac cycle is set based on the R and T waves of the electrocardiogram.

5. The ultrasonic diagnostic apparatus of claim 1, wherein the biomedical signal is represented as a phonocardiogram by a phonocardiograph.

6. The ultrasonic diagnostic apparatus of claim 5, wherein the partial period of the one cardiac cycle is set based on at least one of I,II,III and IV sounds of the phonocardiogram.

7. The ultrasonic diagnostic apparatus of claim 1, wherein the biomedical signal is represented as a sphygmogram by a sphygmograph.

8. The ultrasonic diagnostic apparatus of claim 7, wherein the partial period of the one cardiac cycle is set based on at least one of S, P, T, C and D waves of the sphygmogram.

9. The ultrasonic diagnostic apparatus of claim 1, wherein the computing section calculates in advance a positional displacement waveform, showing the magnitude of positional displacement of the body tissue during the one cardiac cycle, and sets the partial period of the one cardiac cycle based on the positional displacement waveform.

10. The ultrasonic diagnostic apparatus of claim 1, wherein the computing section calculates in advance a thickness variation waveform, showing a variation in the thickness of the body tissue during the one cardiac cycle, according to the magnitude of positional displacement and sets the partial period of the one cardiac cycle based on the thickness variation waveform.

11. The ultrasonic diagnostic apparatus of claim 1, wherein the computing section calculates in advance a vascular caliber variation waveform, showing a variation in the vascular caliber of the body tissue during the one cardiac cycle, according to the magnitude of positional displacement and sets the partial period of the one cardiac cycle based on the vascular caliber variation waveform.

12. The ultrasonic diagnostic apparatus of claim 1, wherein the partial period accounts for 5% to 75% of the one cardiac cycle.

13. The ultrasonic diagnostic apparatus of claim 1, further comprising a display section for displaying the greatest thickness difference and/or elastic property,
   wherein the computing section calculates the greatest thickness difference and/or elastic property during the rest of the one cardiac cycle after the partial period has expired, and
   wherein the display section starts to display the greatest thickness difference and/or elastic property during the one cardiac cycle including the partial period.

14. The ultrasonic diagnostic apparatus of claim 13, wherein the transmitting section drives the ultrasonic probe during the partial period of the one cardiac cycle and stops driving the ultrasonic probe during the rest of the one cardiac cycle.

15. The ultrasonic diagnostic apparatus of claim 1, wherein the circulatory organ is a blood vessel having a vascular wall, and the plurality of measuring points are located inside vascular wall tissue.

16. A method for controlling an ultrasonic diagnostic apparatus which comprises a transmitting section, a receiving section, a phase detecting section and computing section, by a control section of the apparatus, the method comprising the steps of:

controlling the transmitting section and the receiving section by the control section to transmit an ultrasonic wave and receive an ultrasonic reflected wave, which is produced by getting the ultrasonic wave reflected by a body tissue of an organism;

controlling the phase detecting section by the control section to detect the phase of the ultrasonic reflected wave; and controlling the computing section by the control section to calculate the magnitudes of positional displacement at a plurality of measuring points inside the body tissue, wherein each measuring point is spaced apart in a depth direction with respect to a surface of the body tissue relative to each other measuring point, based on a signal obtained by the phase detecting step and also to figure out an elastic property between two of the measuring points based on the magnitudes of positional displacement, wherein the body tissue is a circulatory organ, wherein the step of controlling the computing section includes figuring out the maximum and minimum values of thicknesses or thickness variations between the two points based on the magnitudes of positional displacement at the two points during a measuring period set as a predetermined partial period shorter than one cardiac cycle of the organism, calculating the greatest thickness difference between the maximum and minimum thickness or thickness variations, receiving information about a blood pressure value of the organism and also calculating the elastic property based on the greatest thickness difference and the blood pressure value, and wherein the partial period of the one cardiac cycle is set in sync with a biomedical signal obtained from the organism.

17. The method of claim 16, further comprising the step of displaying the greatest thickness difference and/or elastic property, wherein the step of computing includes calculating the greatest thickness difference and/or elastic property during the rest of the one cardiac cycle after the partial period has expired, and wherein the step of displaying includes starting to display the greatest thickness difference and/or elastic property during the one cardiac cycle including the partial period.

18. The method of claim 16, wherein the circulatory organ is a blood vessel having a vascular wall, and the plurality of measuring points are located inside vascular wall tissue.

* * * * *